(12) United States Patent
Seo et al.

(10) Patent No.: US 10,123,773 B2
(45) Date of Patent: Nov. 13, 2018

(54) REMOTELY CONTROLLED ECHOGRAPHIC APPARATUS

(71) Applicant: KOREA INSTITUTE OF MACHINERY & MATERIALS, Daejeon (KR)

(72) Inventors: Joon-Ho Seo, Daegu (KR); Jang-Ho Cho, Daegu (KR); Hyun-Soo Woo, Daegu (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 521 days.

(21) Appl. No.: 14/966,823

(22) Filed: Dec. 11, 2015

(65) Prior Publication Data
US 2016/0228093 A1 Aug. 11, 2016

(30) Foreign Application Priority Data
Feb. 11, 2015 (KR) ........................ 10-2015-0020812

(51) Int. Cl.
*A61B 8/00* (2006.01)
*A61B 34/30* (2016.01)
*A61B 8/14* (2006.01)

(52) U.S. Cl.
CPC .............. *A61B 8/4461* (2013.01); *A61B 8/54* (2013.01); *A61B 8/582* (2013.01); *A61B 34/30* (2016.02); *A61B 8/14* (2013.01); *A61B 8/4455* (2013.01); *A61B 8/565* (2013.01); *A61B 2034/304* (2016.02)

(58) Field of Classification Search
CPC ......... A61B 8/4461; A61B 8/582; A61B 8/54; A61B 34/30; A61B 8/565; A61B 2034/304; A61B 8/14; A61B 8/4455
See application file for complete search history.

(56) References Cited

U.S. PATENT DOCUMENTS

2014/0135611 A1  5/2014  Loustaudaudine

FOREIGN PATENT DOCUMENTS

JP  2005204696 A  *  8/2005  .............. A61B 8/00

\* cited by examiner

*Primary Examiner* — Joel Lamprecht
(74) *Attorney, Agent, or Firm* — Hauptman Ham, LLP

(57) ABSTRACT

An echographic apparatus includes a base frame, a driving part, an upper frame, a connecting frame, an echographic probe, a grasping part and a connecting part. The base frame has a first opening portion. The driving part is fixed to the base frame and generates a driving power. The upper frame has a second opening portion, and is disposed over the base frame. The connecting frame is fixed to an upper surface of the upper frame. The echographic probe makes contact with a body of a patient through the first opening portion to diagnose the patient. The grasping part is fixed to the connecting frame through the second opening portion, and grasps the echographic probe. The connecting part is connected between the driving part and the upper frame, and transfers the driving power of the driving part to change a position or a posture of the echographic probe.

14 Claims, 8 Drawing Sheets

REMOTELY CONTROLLED ECHOGRAPHIC APPARATUS

PRIORITY STATEMENT

This application claims priority under 35 U.S.C. § 119 to Korean Patent Application No. 10-2015-0020812, filed on Feb. 11, 2015, and all the benefits accruing therefrom, the content of which is herein incorporated by reference in its entirety.

BACKGROUND

1. Field of Disclosure

The present disclosure of invention relates to an echographic apparatus. More particularly, the present disclosure of invention relates to an echographic apparatus having multi degrees of freedom and remotely controlled by a health care provider for echography.

2. Description of Related Technology

Echography is one of diagnoses for a patient, and is performed by a health care provider as a doctor having a professional anatomic knowledge for analyzing medical results. Thus, the health care provider as the doctor should be involved in a field of performing echography.

However, the professional health care provider is hard to be involved in every field of performing echography like an isolated area, an emergency place and so on. Thus, echography is necessary to be remotely controlled, or echography is necessary to be performed by an echographic robot or an echographic apparatus.

The echographic robot or the echographic apparatus may be manufactured with a relatively smaller size compared to other kinds of diagnosing apparatuses, so that the echographic robot or the echographic apparatus may be easily used in the isolated area or the emergency place as a potable. Accordingly, the portable echographic robot or the portable echographic apparatus may be used more widely like the isolated area, the emergency place and so on, with remotely controlled and remotely diagnosed by the professional health care provider.

Regarding the remotely echographic robot or the echographic apparatus, Loustaudaudine (US 2014/0135611) discloses a robotized system for moving a remotely guided tool having four degrees of freedom.

However, in the robotized system disclosed by Loustaudaudine, an echographic probe extends from one side and thus the robotized system is less stabilized and is hard to be precisely controlled. In addition, a power is transferred via a gear combination, so that a control velocity may be decreased or the degrees of freedom may be limited. Thus, the robotized system is hard to be precisely controlled.

SUMMARY

The present invention is developed to solve the above-mentioned problems of the related arts. The present invention provides an echographic apparatus having multi degrees of freedom to be precisely and effectively controlled, and being portably manufactured to be remotely controlled by a health care provider.

According to an example embodiment, an echographic apparatus includes a base frame, a driving part, an upper frame, a connecting frame, an echographic probe, a grasping part and a connecting part. The base frame has a first opening portion in a central portion thereof. The driving part is fixed to the base frame and generates a driving power. The upper frame has a second opening portion in a central portion thereof, and is disposed over the base frame. The connecting frame is fixed to an upper surface of the upper frame. The echographic probe makes contact with a body of a patient through the first opening portion to diagnose the patient. The grasping part is fixed to the connecting frame through the second opening portion, and grasps the echographic probe. The connecting part is connected between the driving part and the upper frame, and transfers the driving power of the driving part to change a position or a posture of the echographic probe.

In an example embodiment, the driving part may include a driving motor, and a driving axis of the driving motor may extend parallel with the base frame toward the first opening portion.

In an example embodiment, the connecting part may include a rotating rod connected to the driving axis and rotating with the driving axis, and an extending rod may connect the rotating rod with the upper frame. The rotating rod and the extending rod may be connected with a ball joint, and the connecting rod and the upper frame may be connected with a ball joint.

In an example embodiment, the driving part may include a pair of first and second driving parts extending parallel with each other, a pair of third and fourth driving parts extending parallel with each other, and a pair of fifth and sixth driving parts extending parallel with each other. A central portion between the first and second driving parts, a central portion between the third and fourth driving parts, a central portion between the fifth and sixth driving parts, may be arranged in an angle of 120° with respect to a central point of the first opening portion.

In an example embodiment, the connecting part may include first to sixth connecting parts connecting each of the first and sixth driving parts to the upper frame.

In an example embodiment, the upper frame may include a first rod fixing part at which the first and second connecting parts are fixed, a second rod fixing part at which the third and fourth connecting parts are fixed, and a third rod fixing part at which the fifth and sixth connecting part are fixed.

In an example embodiment, the first to third rod fixing parts may be arranged in an angle of 120° with respect to the central point of the first opening portion.

In an example embodiment, the echographic apparatus may further include a gripping part fixed to the base frame and extending to outside In an example embodiment, the connecting frame may include a protruding portion protruding to a lower direction, and the upper frame may have an upper hole into which the protruding portion is inserted, so that the connecting frame may be fixed to the upper frame.

In an example embodiment, a scrapping hole may be formed through a scrapping connecting surface of the scrapping part and a connecting hole corresponding to the scrapping hole may be formed through the connecting frame, so that the scrapping part and the connecting frame may be fixed with each other via a connecting screw.

In an example embodiment, the scraping part may include first and second scraping units forming a receiving space and connected with each other, and the echographic probe may be scraped in the receiving space by the first and second scraping units.

In an example embodiment, the driving part may be remotely controlled to generate the driving power to remotely control the position or the posture of the echographic probe.

In an example embodiment, a first magnet part may be fixed on a lower surface of the connecting frame, and a second magnet part may be fixed on a upper surface of the upper frame, so that the connecting frame and the upper frame may be attached with each other via a magnetic force.

In an example embodiment, a force applied to the echographic probe may be transferred to the connecting frame through the grasping part. The connecting frame may be detached from the upper frame when the force applied to the echographic probe is larger than the magnetic force applied between the connecting frame and the upper frame.

According to the example embodiments of the present invention, the echographic probe is controlled to have at least six degrees of freedom at the position or the posture of the echographic probe, the position or the posture of the echographic probe is not limited due to an interference in using the echographic apparatus, and thus the patient may be more effectively and easily diagnosed.

The probe is remotely controlled, and thus the patient may be diagnosed even though the patient is isolated or far from the professional health care provider. Thus, the remotely echographic apparatus may be easily and effectively used with carried by a patient or an ordinary person without a limitation of usage.

Here, the gripping part extends from the base frame, and thus users grasps the gripping part and fixes the base frame at a diagnosis position. Thus, the echographic apparatus may be used more efficiently, accurately and easily.

In addition, a pair of the driving motors of the driving part include a pair of driving axes extending along the same direction, a pair of connecting parts symmetrically extending with each other are connected to the pair of driving axes, the pair of connecting parts are fixed to one rod fixing part, and each pair of driving motors among six driving motors and each pair of connecting parts among six connecting parts are arranged in an angle of 120°. Thus, the echographic probe fixed from the upper frame may uniformly move to every direction with six degrees of freedom, and the echographic probe may rotate with respect to an axis in which the echographic probe extends. Accordingly, the patient may be more effectively and accurately diagnosed, and the echographic probe may move with less interference due to the connecting parts.

In addition, the echographic probe is grasped by the grasping part, and the grasping part may be detached from the connecting part, so that the echographic probe may be easily repaired or changed. Further, various kinds of echographic probes may be easily equipped so that a proper diagnosis may be performed considering a state of the patient.

Alternatively, the connecting frame and the upper frame are attached via a magnetic force, and the echographic apparatus may have a relatively simple connecting structure.

When the force applied to the echographic probe is larger than the magnetic force, the connecting frame connected to the echographic probe is detached from the upper frame, and thus a safe of the patient may be guaranteed. When the force applied to the echographic probe is larger, the patient may feel a pain or a bad condition. Thus, connecting frame connected to the echographic probe is detached from the upper frame, to protect the patient safely. Here, a maximum of the magnetic force is controlled to control the maximum allowable force applied to the echographic probe.

BRIEF DESCRIPTION OF THE DRAWINGS

The above and other features and advantages will become more apparent by describing exemplary embodiments thereof with reference to the accompanying drawings, in which.

DETAILED DESCRIPTION

Hereinafter, exemplary embodiment of the invention will be explained in detail with reference to the accompanying drawings.

Figure 1:
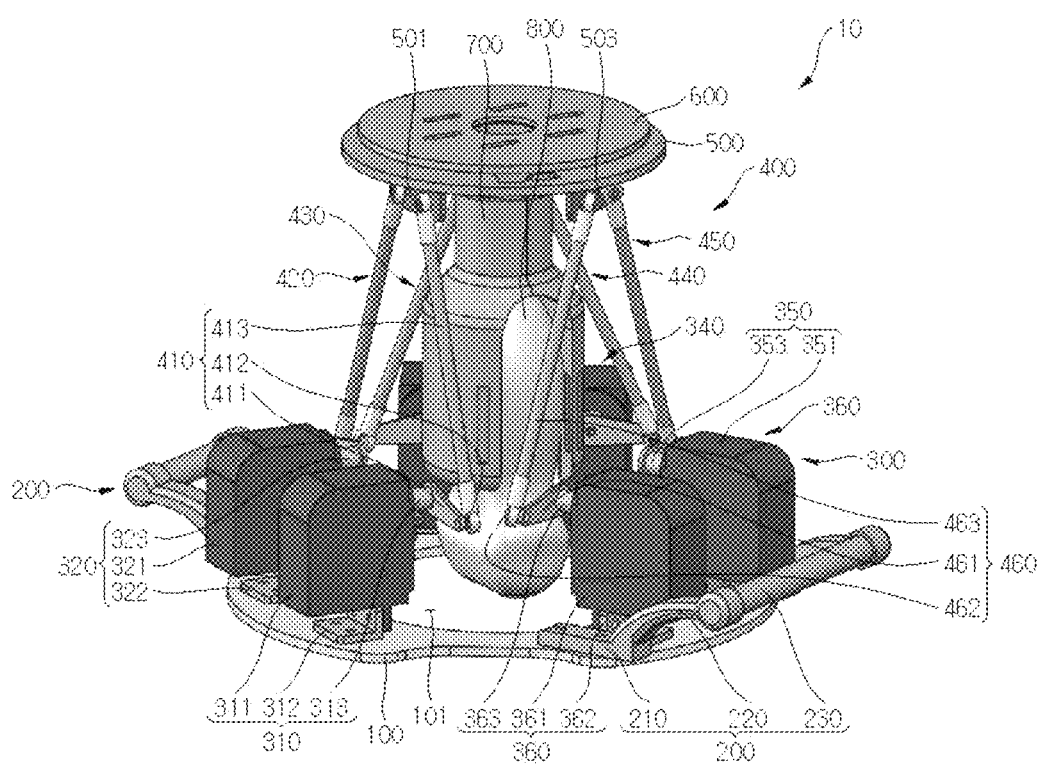
FIG. 1 is a perspective view illustrating an echographic apparatus according to an example embodiment of the present invention.
Figure 2:
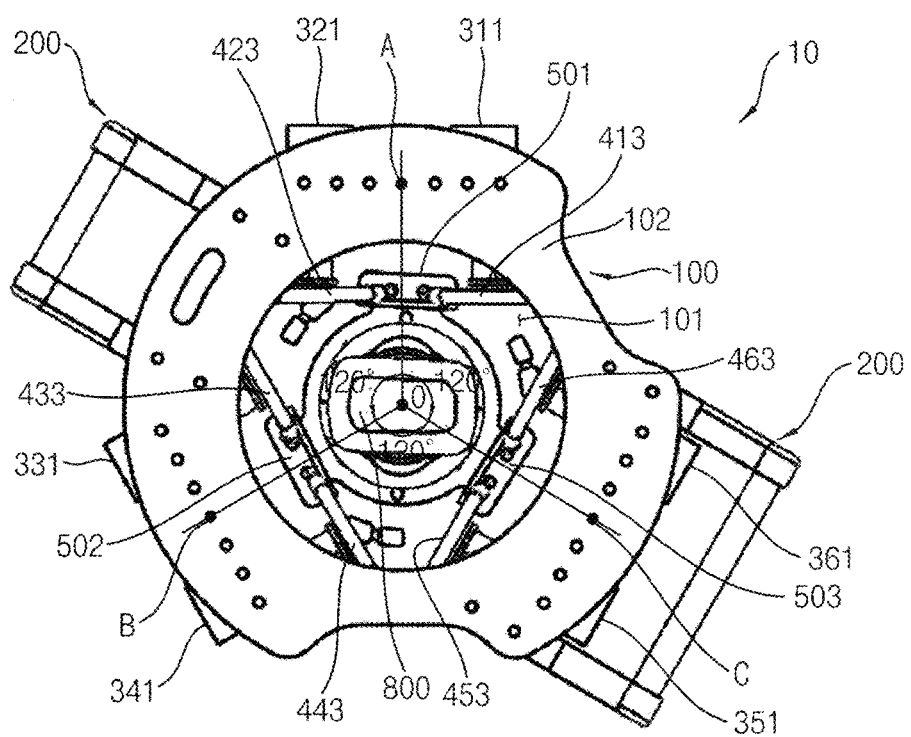
FIG. 2 is a base view illustrating the echographic apparatus of FIG. 1.
Figure 3:
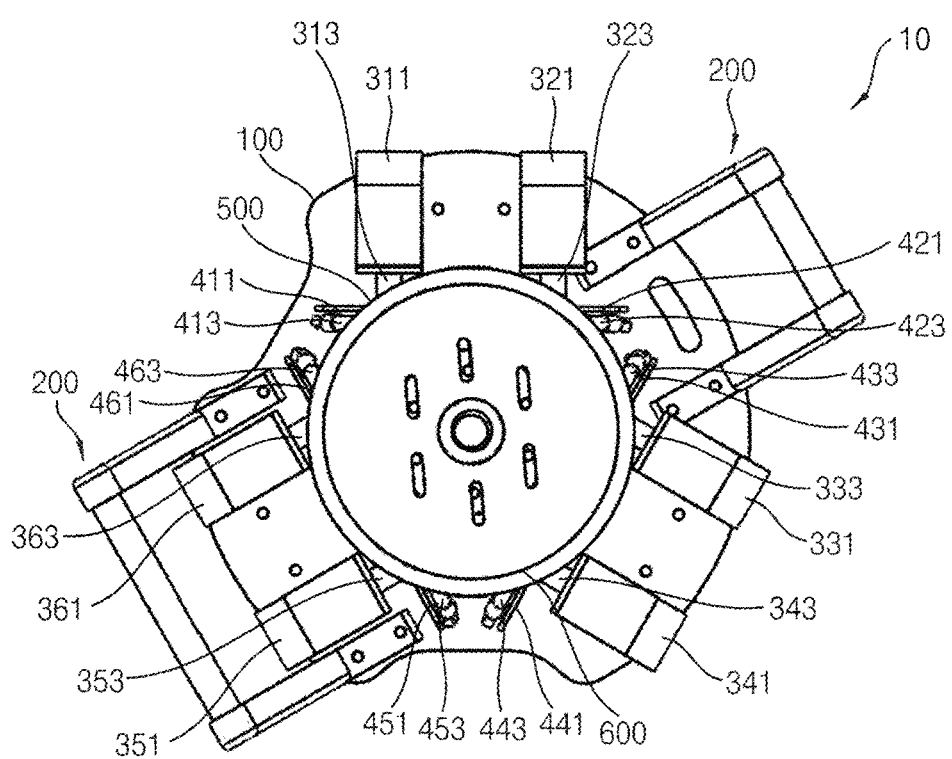
FIG. 3 is a plan view illustrating the echographic apparatus of FIG. 1.

FIG. 1 is a perspective view illustrating an echographic apparatus according to an example embodiment of the present invention. FIG. 2 is a base view illustrating the echographic apparatus of FIG. 1. FIG. 3 is a plan view illustrating the echographic apparatus of FIG. 1.

Referring to FIGS. 1, 2 and 3, the echographic apparatus 10 according to the present example embodiment includes a base frame 100, a gripping part 200, a driving part 300, a connecting part 400, an upper frame 500, a connecting frame 600, a grasping part 700 and an echographic probe 800.

The base frame 100 has a plate shape, and a first opening portion 101 is formed through the base frame 100. As illustrated in FIG. 2, the base frame 100 may have a circular plate shape having an opening portion at a center of the base frame 100, and a circumference of the base frame 100 partially caves in.

Alternatively, the base frame 100 may have various kinds of plate shapes with the first opening portion 101 formed through the base frame 100 at a center of the base frame 100.

A base surface 102 of the base frame 100 makes contact with a body skin of the patient. Thus, the patient is diagnosed by the echographic probe 800 passing through the first opening portion 101, with the base surface 102 making contact with the body skin of the patient.

The base frame 100 makes contact with and is fixed to the body skin of the patient.

The gripping part 200 is fixed on an upper surface of the base frame 100, and a pair of the gripping parts is symmetrically disposed. Thus, a user grasps the pair of the gripping parts with both hands, and disposes the base frame 100 to make contact with the body skin of the patient.

The gripping part 200 includes a gripping fixing portion 210 fixed on the upper surface of the base frame 100, a gripping extending portion 220 extending outside of the base frame 100 from the gripping fixing portion 210, and a gripping portion 230 connected from the gripping extending portion 200 and grasped by the user.

The driving part 300 is fixed on the upper surface of the base frame 100, and provides a driving power. Here, the driving part 300 is remotely controlled to generate the driving power, and additional wire or wireless network systems (not shown) may be equipped.

In the present example embodiment, the driving part 300 includes first to sixth driving parts 310, 320, 330, 340, 350 and 360. The first to sixth driving parts 310, 320, 330, 340, 350 and 360 respectively include first to sixth driving motors 311, 321, 331, 341, 351 and 361, first to sixth motor fixing parts 312, 322, 332, 342, 352 and 362, and first to sixth driving axes 313, 323, 333, 343, 353 and 363.

Each of the first to sixth driving parts has substantially same shape and performance except for an arranging position and a posture.

In the present example embodiment, the first and second driving parts 310 and 320 are a pair and disposed with substantially same posture. Likewise, the third and fourth driving parts 330 and 340 are a pair and disposed with substantially same posture, and the fifth and sixth driving parts 350 and 360 are a pair and disposed with substantially same posture.

The first and second driving parts 310 and 320 are disposed adjacent to each other. The first and second driving axes 313 and 323 head for the first opening portion 101, and extend parallel with each other. Here, the first and second driving axes 313 and 323 extend parallel with an extending direction of the base frame 100.

Likewise, the third and fourth driving parts 330 and 340 are disposed adjacent to each other. The third and fourth driving axes 333 and 343 head for the first opening portion 101, extend parallel with each other, and extend parallel with the extending direction of the base frame 100.

In addition, the fifth and sixth driving parts 350 and 360 are disposed adjacent to each other. The fifth and sixth driving axes 353 and 363 head for the first opening portion 101, extend parallel with each other, and extend parallel with the extending direction of the base frame 100.

In addition, a first central portion A which is a center between the first and second driving parts 310 and 320, a second central portion B which is a center between the third and fourth driving parts 330 and 340, and a third central portion C which is a center between the fifth and sixth driving parts 350 and 360, form three apexes of the equilateral triangle, and are disposed with an angle of 120° with respect to a central point O of the first opening portion 101.

Thus, the pair of first and second driving parts 310 and 320, the pair of third and fourth driving parts 330 and 340, and the pair of fifth and sixth driving parts 350 and 360, are symmetrically disposed with an angle of 120° with respect to the central point O and correspond to three apexes of the equilateral triangle.

The connecting part 400 includes first to sixth connecting parts 410, 420, 430, 440, 450 and 460 respectively corresponding to the first and sixth driving parts 310, 320, 330, 340, 350 and 360.

The first to sixth connecting parts 410, 420, 430, 440, 450 and 460 respectively includes first to sixth rotating rods 411, 421, 431, 441, 451 and 460, first to sixth extending rods 413, 423, 433, 443, 453 and 463, and first to sixth connecting units 412, 422, 432, 442, 452 and 462. The first to sixth rotating rods 411, 421, 431, 441, 451 and 460 are connected to the first to sixth driving axes 313, 323, 333, 343, 353 and 363, and rotate with respect to the first to sixth driving axes 313, 323, 333, 343, 353 and 363, respectively. The first to sixth extending rods 413, 423, 433, 443, 453 and 463 are respectively connected between the upper frame 500 and the first to sixth rotating rods 411, 421, 431, 441, 451 and 460. The first to sixth connecting units 412, 422, 432, 442, 452 and 462 respectively connecting the first to sixth rotating rods 411, 421, 431, 441, 451 and 460 to the first to sixth extending rods 413, 423, 433, 443, 453 and 463.

Here, each of the first to sixth connecting units 412, 422, 432, 442, 452 and 462 may be a ball joint, and thus the first to sixth rotating rods 411, 421, 431, 441, 451 and 461 may be respectively connected with the first to sixth extending rods 413, 423, 433, 443, 453 and 463 with a various kinds of connecting angles.

First ends of the first to sixth rotating rods 411, 421, 431, 441, 451 and 461 are respectively fixed to the first to sixth driving axes 313, 323, 333, 343, 353 and 363, and thus the first to sixth rotating rods 411, 421, 431, 441, 451 and 461 respectively rotate by a first distance as the first to sixth driving axes 313, 323, 333, 343, 353 and 363 rotates. Here, the first distance may be defined as a distance of each of the first to sixth rotating rods 411, 421, 431, 441, 451 and 461 which is substantially same with each other.

First ends of the first to sixth extending rods 413, 423, 433, 443, 453 and 463 are respectively connected to second ends of the first to sixth rotating rods 411, 421, 431, 441, 451 and 461. Thus, each of the first to sixth extending rods 413, 423, 433, 443, 453 and 463 moves up and down and changes a position of a portion of the upper frame 500 connected to the first to sixth extending rods 413, 423, 433, 443, 453 and 463, as the first to sixth rotating rods 411, 421, 431, 441, 451 and 461 rotates.

Here, first to third rod fixing parts are fixed to a base surface of the upper frame 500, second ends of the first and second extending rods 413 and 423 are connected to the first rod fixing part 501 with a ball joint, second ends of the third and fourth extending rods 433 and 443 are connected to the second rod fixing part 502, and second ends of the fifth and sixth extending rods 453 and 463 are connected to the third rod fixing part 503.

The pair of first and second extending rods 413 and 432 transfers the driving power provided from the pair of first and second driving parts 310 and 320 to the base surface of the upper frame 500 via the first rod fixing part 501. The pair of third and fourth extending rods 433 and 443 transfers the driving power provided from the pair of third fourth driving parts 330 and 340 to the base surface of the upper frame 500 via the second rod fixing part 502. The pair of fifth and sixth extending rods 453 and 463 transfers the driving power provided from the pair of fifth and sixth driving parts 350 and 360 to the base surface of the upper frame 500 via the third rod fixing part 503.

Here, the first to sixth extending rods 413, 423, 433, 443, 453 and 463 move the first to third rod fixing parts 501, 502 and 503 up and down, and thus the upper plate 500 moves up and down at a position where the first to third rod fixing parts 501, 502 and 503 are fixed.

Since the first to third rod fixing parts 501, 502 and 503 are disposed with an angle of 120° with respect to the central point O of the first opening portion 101 and are respectively disposed at three apexes of the equilateral triangle, the upper plate 500 forms various kinds of planar angle according to the up and down movement of the first to third rod fixing parts 501, 502 and 503.

Accordingly, the echographic probe 800 fixed to the upper plate 500 and extending to a lower direction may be disposed with various kinds of position and posture according to the planar angles of the upper plate 500, and the echographic probe 800 may have at least 6 degrees of freedom.

In the present example embodiment, a rotating power due to the rotation of the first to sixth driving axes is transferred to an up and down moving power via the first to sixth connecting parts, and thus the planar angels of the upper plate 500 may be variously changed. Thus, the echographic probe 800 may have at least 6 degrees of freedom and the position or the posture of the echographic probe 800 may be variously changed.

Since the first to sixth driving parts are fixed to the base frame 100 and the base frame 100 helps the echographic probe 800 to have the degrees of freedom with respect to a reference position where the base frame 100 is fixed on the body skin of the patient, the echographic probe 800 may secure the degrees of freedom enough to diagnose the patient regardless of the shape or the position of the body skin of the patient.

Figure 4:
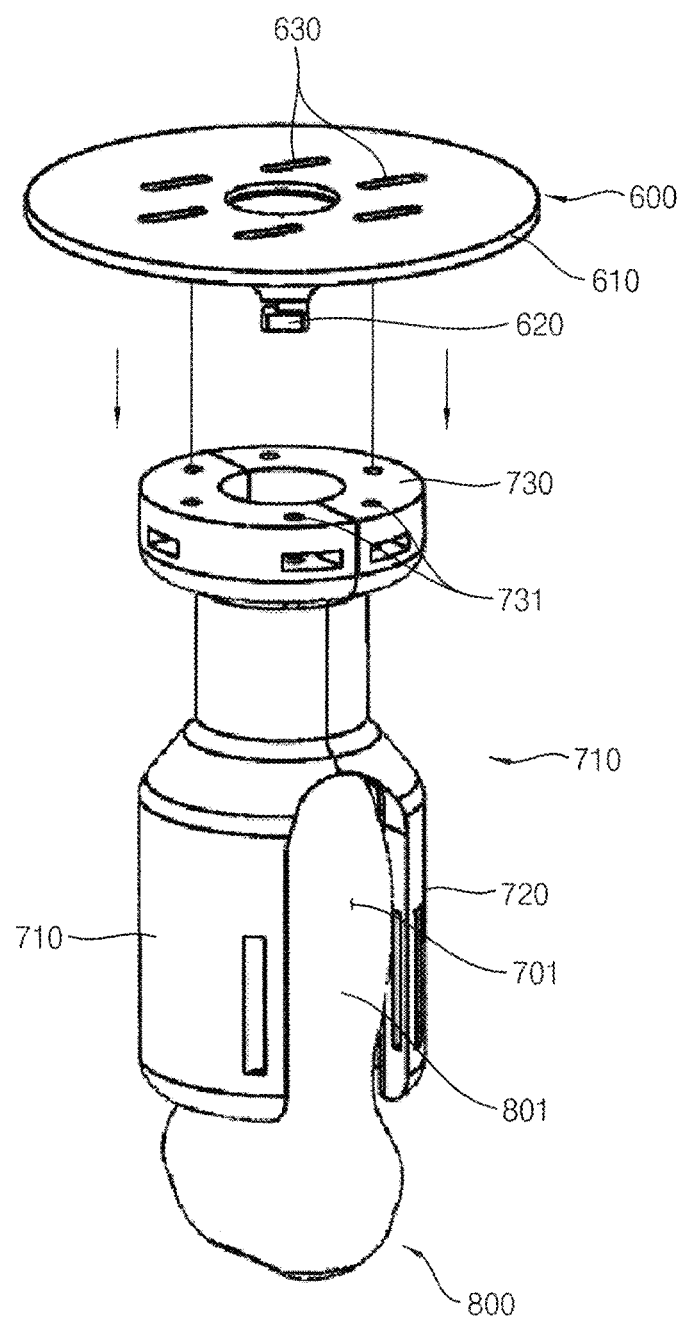
FIG. 4 is a perspective view illustrating a combination between a connecting frame and a grasping part of FIG. 1.
Figure 5:
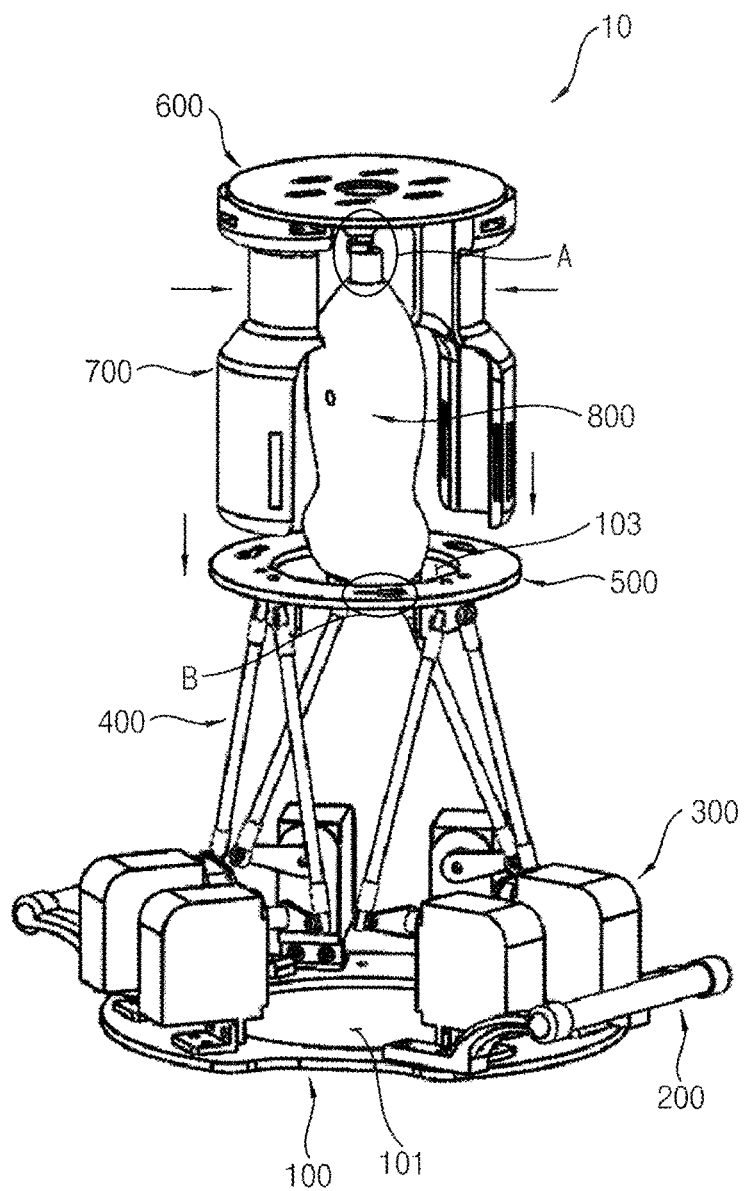
FIG. 5 is a perspective view illustrating a combination between an upper frame and the connecting frame of FIG. 1.
Figure 6A:
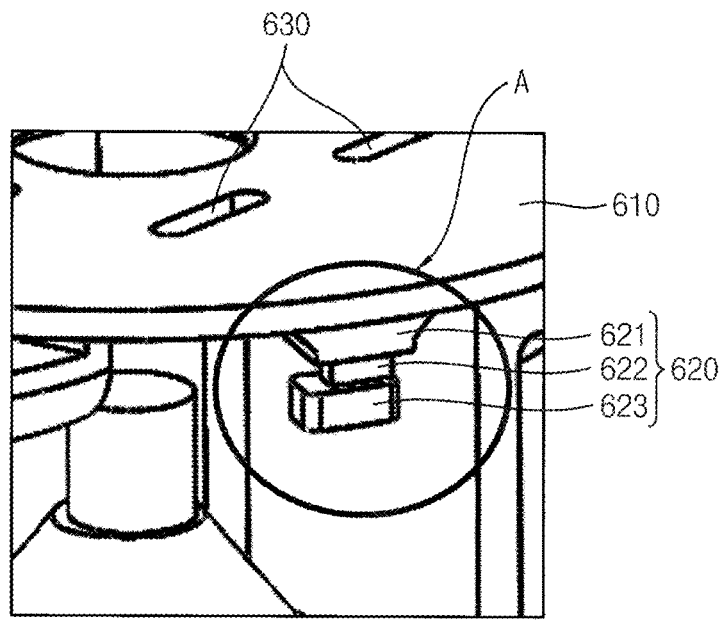
FIG. 6A is a perspective view illustrating a portion 'A'.
Figure 6B:
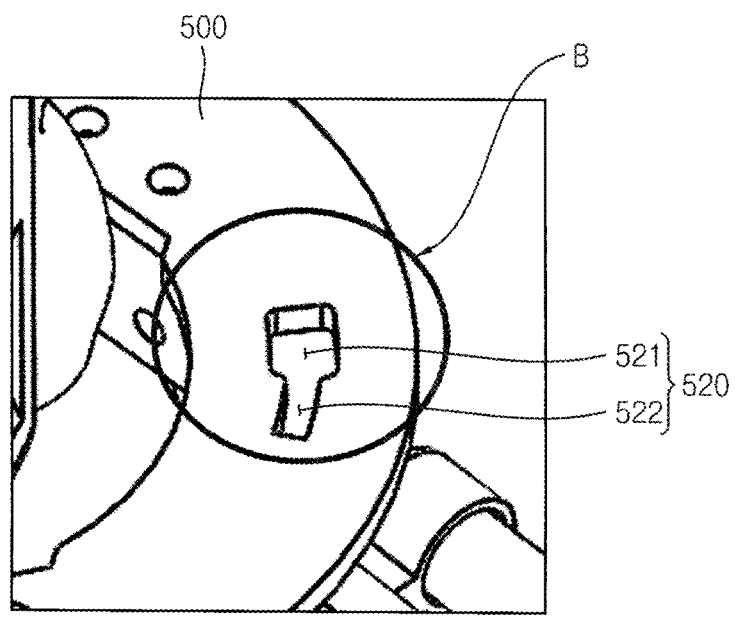
FIG. 6B is a perspective view illustrating a portion 'B'.

FIG. 4 is a perspective view illustrating a combination between a connecting frame and a grasping part of FIG. 1. FIG. 5 is a perspective view illustrating a combination between an upper frame and the connecting frame of FIG. 1. FIG. 6A is a perspective view illustrating a portion 'A', and FIG. 6B is a perspective view illustrating a portion 'B'.

Referring to FIGS. 5 and 6A, the first to third rod fixing parts 501, 502 and 503 are formed on the base surface of the upper frame 500, and a second opening portion 103 is formed through the upper frame 500 at a central portion of the upper frame 500. Thus, the upper frame 500 has a circular plate shape having an opening at the central portion thereof.

In addition, an upper hole 520 having first and second holes 521 and 522 is formed through the upper frame 500. Here, the first and second holes 521 and 522 are connected to each other, and a size of the first hole 521 is larger than that of the second hole 522.

Referring to FIGS. 4, 5 and 6A, the connecting frame 600 is tightly combined to an upper surface 510 of the upper frame 500, and the connecting frame 600 includes a protruding portion 620 protruding to a lower direction.

The protruding portion 620 includes a first protruding portion 621 fixed to a base surface of the connecting frame 600, a second protruding portion 622 extending to the lower direction from the first protruding portion 621, and a third protruding portion 623 extending to the lower direction from the second protruding portion 622.

The protruding portion 620 faces the upper hole 520, and a size of the third protruding portion 623 is larger than that of the second protruding portion 622.

Accordingly, the connecting frame 600 rotates by a predetermined angle for the second protruding portion 622 to be inserted into the second hole 522, with the third protruding portion 623 inserted into the first hole 521, and thus the connecting frame 600 is tightly combined with and fixed to the upper frame 500.

The connecting frame 600 includes a connecting plate 610 having a circular plate shape, and a plurality of connecting holes 630 is formed through the connecting plate 610.

The grasping part 700 grasps the echographic probe 800, and is fixed to the connecting frame 600.

For example, the grasping part 700 includes first and second grasping units 710 and 720, and a grasping connecting surface 730 is formed over the first and second grasping units 710 and 720. The first and second grasping units 710 and 720 face each other and are combined with each other to form a receiving space between the first and second grasping units 710 and 720. The echographic probe 800 is grasped in the receiving space. A plurality of grasping holes 731 is formed through the grasping connecting surface 730 and is arranged in an alignment with the connecting holes 630. Although not shown in the figure, a connecting screw passes through each of the connecting holes 630 and each of the grasping holes 731 to fix the connecting frame 600 with the grasping part 700.

The echographic probe 800 is received by the receiving space 701. Here, each of the first and second grasping parts 710 and 720 is easily detachable, and thus the echographic probe 800 may be easily detached from the receiving space 70 to be easily changed or repaired.

Further, when a shape of a grasping part 801 of the echographic probe 800 grasped by the receiving space 701 is substantially same, an end of the echographic probe 800 may be variously changed. Thus, various kinds of echographic probes may be used considering a body shape of the patient or a diagnosing position of the patient.

Accordingly, the grasping part 700 and the connecting frame 600 fixed with each other, and the echographic probe 800 grasped by the grasping part 700 are disposed between the upper frame 500 and the base frame 100 through the second opening portion 501, and the upper frame 500 and the connecting frame 600 are fixed to each other, so that the remotely echographic apparatus 10 is assembled.

Thus, the position or the posture of the echographic probe 800 may be changed as the position or the posture of the upper frame 500, with the echographic probe 800 positioned over the first opening portion 101, and the echographic probe 800 makes contact with the body skin of the patient through the first opening portion 101, with the base frame 100 making contact with the body skin of the patient.

Figure 7:
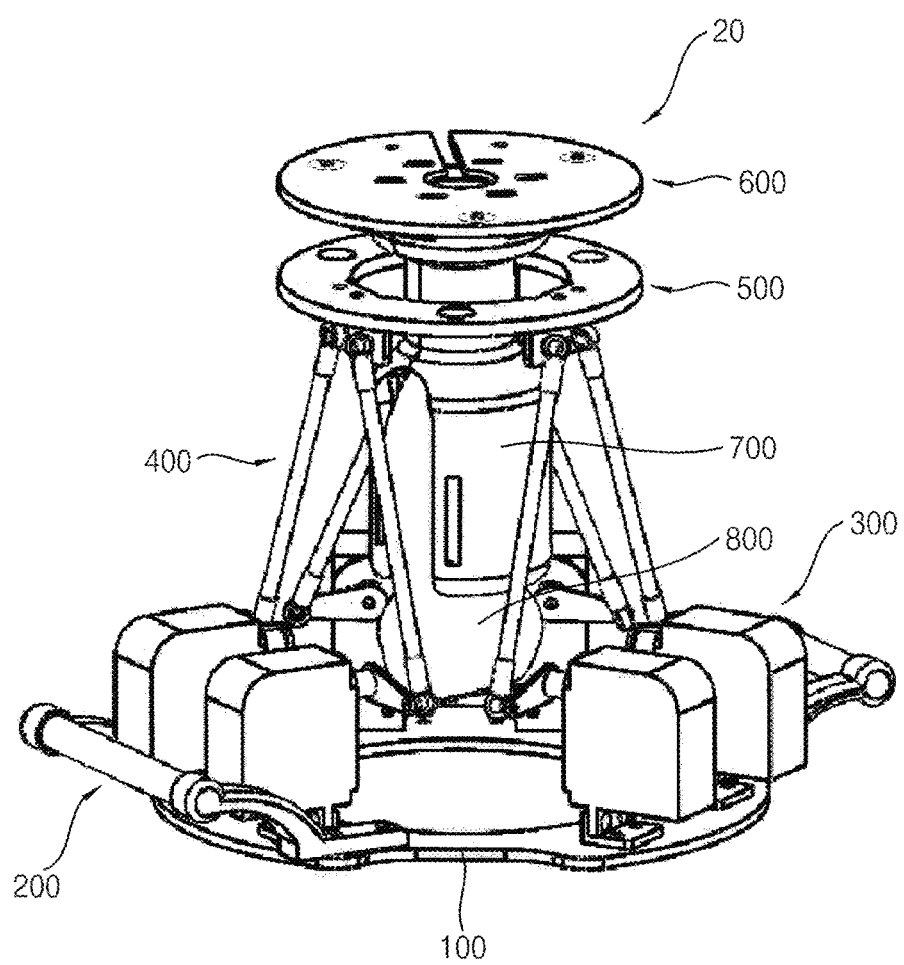
FIG. 7 is a perspective view illustrating an echographic apparatus according to another example embodiment of the present invention.
Figure 8A:
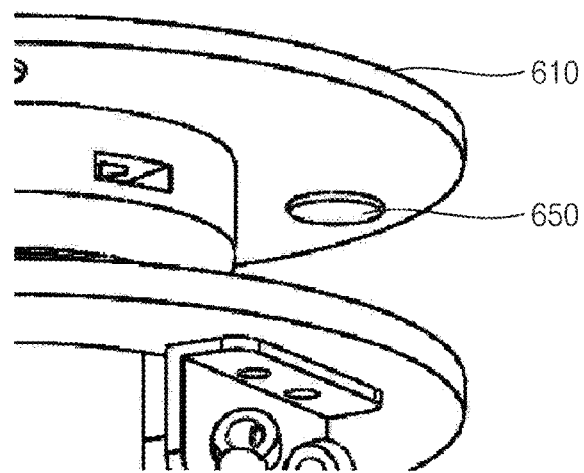
FIGS. 8A and 8B are enlarged perspective view illustrating a connecting frame and an upper frame 500 of FIG. 7.
Figure 8B:
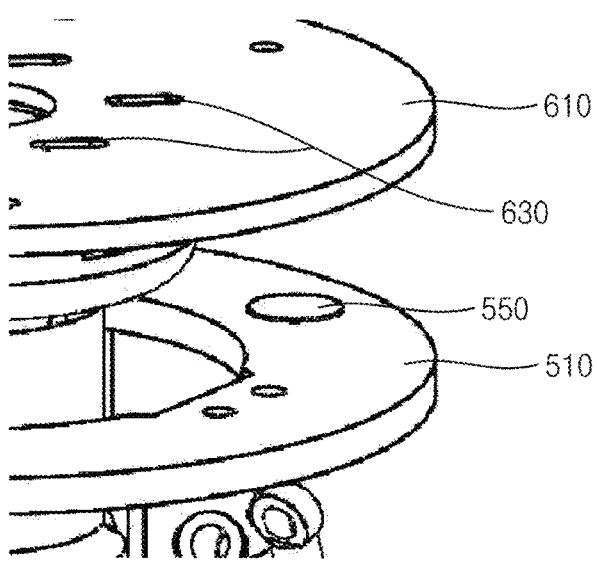

FIG. 7 is a perspective view illustrating an echographic apparatus according to another example embodiment of the present invention. FIGS. 8A and 8B are enlarged perspective view illustrating a connecting frame and an upper frame 500 of FIG. 7.

The echographic apparatus 20 according to the present example embodiment is substantially same as the echographic apparatus 10 in FIGS. 1 to 6B, except that the echographic apparatus 20 includes first and second magnet parts without the protruding portion and the upper hole. Thus, same reference numerals are used and any repetitive explanation will be omitted.

Referring to FIGS. 7, 8A and 8B, in the echographic apparatus 20, a first magnet part 650 is fixed on a lower surface of the connecting plate 610 of the connecting frame 600, and a second magnet part 550 is fixed on the upper surface 510 of the upper frame 500.

Here, a plurality of the first magnet parts 650 may be arranged by a predetermined distance, and a plurality of the second magnet parts 550 may be arranged by a predetermined distance. In addition, the first magnet parts 650 respectively face the second magnet parts 550, and each of the first and second magnet parts 650 and 550 adheres to each other via a magnetic force.

Here, a maximum allowable magnetic force between the first and second magnet parts 650 and 550 may be controlled or preset considering the required magnetic force.

As explained above, the echographic probe 800 is fixed to the grasping part 700, and is connected to the connecting frame 600.

Thus, when diagnosing the patient, a force applied to the echographic probe 800 is directly transferred to the connecting frame 600. As illustrated in FIG. 7, the force upwardly applied to the echographic probe 800 is directly transferred to the connecting frame 600, and thus the force is applied along an opposite direction to the magnetic force between the connecting frame 600 and the upper frame 500.

When the force upwardly applied to the echographic probe 800 is larger than the magnetic force between the connecting frame 600 and the upper frame 500, the connecting frame 600 is detached from the upper frame 500.

Accordingly, in the present example, when the force larger than a predetermined force or a reference force is applied, the connecting frame 600 is detached from the upper frame 500. Thus, the force larger than the predetermined force or the reference force is prevented from being applied to the patient.

When the force larger than the predetermined force or the reference force is applied to the patient via the echographic probe 800, the patient may be in a bad condition or bad effect may be caused to the patient. Thus, the connecting frame 600 is detached from the upper frame 500 to prevent the patient from the larger force applied by the echographic probe 800.

In addition, the maximum allowable magnetic force between the connecting frame 600 and the upper frame 500 may be controlled to control the maximum force applied to the patient.

According to the example embodiments of the present invention, the echographic probe is controlled to have at least six degrees of freedom at the position or the posture of the echographic probe, the position or the posture of the echographic probe is not limited due to an interference in using the echographic apparatus, and thus the patient may be more effectively and easily diagnosed.

The probe is remotely controlled, and thus the patient may be diagnosed even though the patient is isolated or far from the professional health care provider. Thus, the remotely echographic apparatus may be easily and effectively used with carried by a patient or an ordinary person without a limitation of usage.

Here, the gripping part extends from the base frame, and thus users grasps the gripping part and fixes the base frame at a diagnosis position. Thus, the echographic apparatus may be used more efficiently, accurately and easily.

In addition, a pair of the driving motors of the driving part include a pair of driving axes extending along the same direction, a pair of connecting parts symmetrically extending with each other are connected to the pair of driving axes, the pair of connecting parts are fixed to one rod fixing part, and each pair of driving motors among six driving motors and each pair of connecting parts among six connecting parts are arranged in an angle of 120°. Thus, the echographic probe fixed from the upper frame may uniformly move to every direction with six degrees of freedom, and the echographic probe may rotate with respect to an axis in which the echographic probe extends. Accordingly, the patient may be more effectively and accurately diagnosed, and the echographic probe may move with less interference due to the connecting parts.

In addition, the echographic probe is grasped by the grasping part, and the grasping part may be detached from the connecting part, so that the echographic probe may be easily repaired or changed. Further, various kinds of echographic probes may be easily equipped so that a proper diagnosis may be performed considering a state of the patient.

Alternatively, the connecting frame and the upper frame are attached via a magnetic force, and the echographic apparatus may have a relatively simple connecting structure.

When the force applied to the echographic probe is larger than the magnetic force, the connecting frame connected to the echographic probe is detached from the upper frame, and thus a safe of the patient may be guaranteed. When the force applied to the echographic probe is larger, the patient may feel a pain or a bad condition. Thus, connecting frame connected to the echographic probe is detached from the upper frame, to protect the patient safely. Here, a maximum of the magnetic force is controlled to control the maximum allowable force applied to the echographic probe.

The foregoing is illustrative of the present teachings and is not to be construed as limiting thereof. Although a few exemplary embodiments have been described, those skilled in the art will readily appreciate from the foregoing that many modifications are possible in the exemplary embodiments without materially departing from the novel teachings and advantages of the present disclosure of invention. Accordingly, all such modifications are intended to be included within the scope of the present teachings. In the claims, means-plus-function clauses are intended to cover the structures described herein as performing the recited function and not only structural equivalents but also functionally equivalent structures.

What is claimed is:

1. An echographic apparatus comprising:
    a base frame having a first opening portion in a central portion thereof;
    a driving part fixed to the base frame and generating a driving power;
    an upper frame having a second opening portion in a central portion thereof, and disposed over the base frame;
    a connecting frame fixed to an upper surface of the upper frame;
    an echographic probe making contact with a body of a patient through the first opening portion to diagnose the patient;
    a grasping part fixed to the connecting frame through the second opening portion, and grasping the echographic probe; and
    a connecting part connected between the driving part and the upper frame, and transferring the driving power of the driving part to change a position or a posture of the echographic probe.

2. The echographic apparatus of claim 1, wherein the driving part comprises a driving motor, and a driving axis of the driving motor extends parallel with the base frame toward the first opening portion.

3. The echographic apparatus of claim 2, wherein the connecting part comprises a rotating rod connected to the driving axis and rotating with the driving axis, and an extending rod connecting the rotating rod with the upper frame,
    wherein the rotating rod and the extending rod are connected with a ball joint, and the connecting rod and the upper frame are connected with a ball joint.

4. The echographic apparatus of claim 2, wherein the driving part comprises a pair of first and second driving parts extending parallel with each other, a pair of third and fourth driving parts extending parallel with each other, and a pair of fifth and sixth driving parts extending parallel with each other,
    wherein a central portion between the first and second driving parts, a central portion between the third and fourth driving parts, a central portion between the fifth and sixth driving parts, are arranged in an angle of 120° with respect to a central point of the first opening portion.

5. The echographic apparatus of claim 4, wherein the connecting part comprises first to sixth connecting parts connecting each of the first and sixth driving parts to the upper frame.

6. The echographic apparatus of claim 5, wherein the upper frame comprises:

a first rod fixing part at which the first and second connecting parts are fixed;

a second rod fixing part at which the third and fourth connecting parts are fixed; and a third rod fixing part at which the fifth and sixth connecting part are fixed.

7. The echographic apparatus of claim 6, wherein the first to third rod fixing parts are arranged in an angle of 120° with respect to the central point of the first opening portion.

8. The echographic apparatus of claim 1, further comprising a gripping part fixed to the base frame and extending to outside.

9. The echographic apparatus of claim 1, wherein the connecting frame comprises a protruding portion protruding to a lower direction, and the upper frame has an upper hole into which the protruding portion is inserted, so that the connecting frame is fixed to the upper frame.

10. The echographic apparatus of claim 9, wherein a grasping hole is formed through a grasping connecting surface of the grasping part and a connecting hole corresponding to the grasping hole is formed through the connecting frame, so that the grasping part and the connecting frame are fixed with each other via a connecting screw.

11. The echographic apparatus of claim 1, wherein the grasping part comprises first and second grasping units forming a receiving space and connected with each other, and the echographic probe is grasped in the receiving space by the first and second grasping units.

12. The echographic apparatus of claim 1, wherein the driving part is remotely controlled to generate the driving power to remotely control the position or the posture of the echographic probe.

13. The echographic apparatus of claim 1, wherein a first magnet part is fixed on a lower surface of the connecting frame, and a second magnet part is fixed on a upper surface of the upper frame, so that the connecting frame and the upper frame are attached with each other via a magnetic force.

14. The echographic apparatus of claim 13, wherein a force applied to the echographic probe is transferred to the connecting frame through the grasping part, wherein the connecting frame is detached from the upper frame when the force applied to the echographic probe is larger than the magnetic force applied between the connecting frame and the upper frame.

\* \* \* \* \*